US00PP35648P3

(12) United States Plant Patent
Meilland

(10) Patent No.: US PP35,648 P3
(45) Date of Patent: Feb. 13, 2024

(54) BEDDING ROSE PLANT NAMED 'MEICONFIZ'

(50) Latin Name: *Rosa hybrida*
Varietal Denomination: MEICONFIZ

(71) Applicant: The Conard Pyle Company, West Grove, PA (US)

(72) Inventor: Alain Antoine Meilland, Antibes (FR)

(73) Assignee: THE CONARD PYLE COMPANY, West Grove, PA (US)

( * ) Notice: Subject to any disclaimer, the term of this patent is extended or adjusted under 35 U.S.C. 154(b) by 36 days.

(21) Appl. No.: 18/134,761

(22) Filed: Apr. 14, 2023

(65) Prior Publication Data

US 2023/0389455 P1 Nov. 30, 2023

(30) Foreign Application Priority Data

May 25, 2022 (QZ) ..... PBR 2022/1313

(51) Int. Cl.
*A01H 5/02* (2018.01)
*A01H 6/74* (2018.01)

(52) U.S. Cl.
USPC ..... Plt./105
CPC ..... *A01H 6/749* (2018.05)

(58) Field of Classification Search
USPC ..... Plt./105, 101
CPC ..... A01H 5/0222
See application file for complete search history.

(56) References Cited

U.S. PATENT DOCUMENTS

PP16,202 P2 1/2006 Radler

*Primary Examiner* — Kent L Bell

(74) *Attorney, Agent, or Firm* — Panitch Schwarze Belisario & Nadel LLP; Stephany G. Small; Travis W. Bliss

(57) ABSTRACT

A new and distinct variety of bedding rose plant, referred to by its cultivar name, 'MEICONFIZ', is disclosed. The new variety forms attractive, double orange-colored flowers. Attractive dark, glossy foliage is formed, which contrasts beautifully with the blossoms. A bushy growth habit is displayed. The new variety is well suited for providing attractive ornamentation in the landscape.

1 Drawing Sheet

Latin name of genus and species of plant claimed: *Rosa hybrida.*

Variety denomination: 'MEICONFIZ'.

CROSS REFERENCE TO RELATED APPLICATIONS

This application claims priority to Plant Breeders' Right Application Number 2022/1313, which was filed at Community Plant Variety Office in the European Union on May 25, 2022, the contents of which are hereby incorporated by reference for all purposes.

STATEMENT REGARDING PRIOR DISCLOSURES BY THE INVENTOR

The first offer for sale of the new variety was Jun. 14, 2022, in the Netherlands. The first offer for sale of the new variety was by the inventor or another who obtained the new variety directly or indirectly from the inventor. No plants of the new variety have been sold in this country or anywhere in the world, nor has any disclosure of the new plant been made, more than one year prior the effective filing date of this application, and such sale or disclosure within one year was either derived directly or indirectly from the inventor.

BACKGROUND OF THE INVENTION

The new variety of rose plant of the present invention was created by controlled breeding at Le Cannet des Maures, Var, France by artificial pollination wherein two parents were crossed which previously had been studied in the hope that they would contribute the desired characteristics. The female parent (i.e., the seed parent) of the new variety was the 'MEINEYTA' variety (not patented). The male parent (i.e., the pollen parent) of the new variety was an unnamed seedling (not patented) that is the product of the cross between an unnamed seedling (not patented) and the 'RADTKO' variety (U.S. Plant Pat. No. 16,202).

The parentage of the new variety can be summarized as follows:

'MEINEYTA' X (Unnamed Seedling x 'RADTKO')

The seeds resulting from the above pollination were sown and small plants were obtained which were physically and biologically different from each other. Selective study resulted in the identification of a single plant of the new variety.

The new variety has been found to undergo asexual propagation in Le Cannet des Maures, Var, France by a number of routes, including eye budding, softwood cuttings, semi-hardwood cuttings, and hardwood cuttings. Asexual propagation by the above-mentioned techniques in Le Cannet des Maures, Var, France has shown that the characteristics of the new variety are stable and are strictly transmissible by asexual propagation from one generation to another. Accordingly, the new variety undergoes asexual propagation in a true-to-type manner.

SUMMARY OF THE INVENTION

It was found that the new variety of rose plant of the present invention possesses the following combination of characteristics:

(a) forms very nice orange-colored flowers, (b) produces double flowers, and (c) exhibits a bushy growth habit.

The new variety well meets the needs of the horticultural industry. It can be grown to advantage as ornamentation in parks, gardens, public areas, and in residential settings. Accordingly, the plant is particularly well suited for growing in the landscape.

The new variety of the present invention can readily be distinguished from its ancestors. More specifically, the 'MEINEYTA' variety (i.e., the seed parent) is less tolerant to disease compared to the new variety. In addition, the unnamed male parent (i.e., pollen parent) produces flowers that are smaller in size and have less petals compared to the new variety. Moreover, the new variety can be readily distinguished from other similar non-parental varieties. For example, the 'MEISHAMALO' variety (not patented) produces a less compact growth habit compared to the new variety.

The new variety has been named 'MEICONFIZ'.

BRIEF DESCRIPTION OF THE PHOTOGRAPH

The accompanying photograph of the drawing shows as nearly true as it is reasonably possible to make the same, in a color illustration of this character, typical specimens of the plant parts of the new variety. The rose plants of the new variety were approximately two years of age and were observed during April while budded by cuttings and growing outdoors at Le Cannet des Maures, Var, France. Dimensions in centimeters are indicated at the bottom of the drawing.

Element 1—illustrates a specimen of a young shoot.

Element 2—illustrates a specimen of a floral bud before the opening of the sepals.

Element 3—illustrates a specimen of a floral bud at the opening of the sepals.

Element 4—illustrates a specimen of a floral bud at the opening of the petals.

Element 5—illustrates a specimen of a flower in the course of opening.

Element 6—illustrates a specimen of an open flower—plan view—obverse.

Element 7—illustrates a specimen of an open flower—plan view—reverse.

Element 8—illustrates a specimen of a fully open flower—plan view—obverse.

Element 9—illustrates a specimen of a fully open flower—plan view—reverse.

Element 10—illustrates a specimen of a floral receptacle showing arrangement of the stamens and pistils.

Element 11—illustrates a specimen of a floral receptacle showing arrangement of the pistils (stamens removed).

Element 12—illustrates a specimen of a flowering stem.

Element 13—illustrates a specimen of a leaf with 3 leaflets—plan view—upper surface.

Element 14—illustrates a specimen of a leaf with 3 leaflets—plan view—under surface.

Element 15—illustrates a specimen of a leaf with 5 leaflets—plan view—upper surface.

Element 16—illustrates a specimen of a leaf with 5 leaflets—plan view—under surface.

Element 17—illustrates a specimen of a leaf with 7 leaflets—plan view—upper surface.

Element 18—illustrates a specimen of a leaf with 7 leaflets—plan view—under surface.

DETAILED BOTANICAL DESCRIPTION

The chart used in the identification of the colors is that of The Royal Horticultural Society (The R.H.S. Colour Chart, 2001 edition), London, England. The terminology which precedes reference to the chart has been added to indicate the corresponding color in more common terms. The description is based on the observation of two-years-old specimens of the new variety during April while budded by cuttings and growing outdoors at Le Cannet des Maures, Var, France.

Botanical classification: *Rosa hybrida* cultivar 'MEICONFIZ'.

Commercial classification: Bedding Rose Plant.

Plant:

*Habit*.—Bushy.

*Height*.—Approximately 50 cm on average.

*Width*.—Approximately 50 cm on average.

Branches:

*Color*.—Young stems: commonly near Yellow-Green Group 144A. — adult wood: commonly near Yellow-Green Group 146A amply suffused with Yellow-Green Group 147A.

*Length*.—From the crown to the flower is approximately 23 cm on average.

*Diameter*.—Typically between 0.3 cm to 0.5 cm.

*Thorns*.—Configuration on adult stems: rather upright, elongated and curved downwards on the upper surface and concave on the under surface. — long prickles — quantity: typically between 5 to 8 thorns on average per 10 cm long young stem and typically between 10 to 15 thorns on average per 10 cm long adult stem. — long prickles — length: typically between 0.5 cm to 1.0 cm on young stems and typically between 0.7 cm to 1.2 cm on adult stems. — long prickles — width at base: approximately 0.2 cm on young stems and approximately 0.2 cm on average on adult stems. — long prickles — base shape: upright elliptical on young stems and on adult stems. — long prickles — color on young stems: commonly near Yellow-Green Group 144B more or less suffused with Greyed-Purple Group 178A at the top. — long prickles — color on adult stems: commonly near Yellow-Green Group 144B amply suffused with Greyed-Purple Group 178A. — small prickles — quantity: absent.

*Internode*.—Numbers on the entire branch: approximately 7 on average. — length: approximately 2.5 cm on average.

Foliage:

*General appearance*.—Dense, dark and glossy.

*Number of leaflets*.—3, 5, 7; most often 5.

5 *leaflets leaf*.—Length: approximately 10.0 cm on average. — width: approximately 7.5 cm on average.

*Terminal leaflet*.—Length: approximately 4.0 cm on average. — width: approximately 3.0 cm on average.

*Young shoots*.—Anthocyanin coloration: upper surface is commonly near Greyed-Purple Group 178A; absent on under surface.

*New foliage*.—Upper surface color: commonly near a color between Yellow-Green Group 146A and Yellow-Green Group 147A. — under surface color: commonly near a color between Yellow-Green Group 146A and Yellow-Green Group 146B.

*Adult foliage*.—Upper surface color: commonly near Yellow-Green Group 147A. — under surface color: commonly near Yellow-Green Group 147B.

Leaflets:

*Shape*.—Tip: acuminate. — base: obtuse.

*Intensity of glossiness*.—Very strong.

*Texture*.—Upper surface is smooth; under surface is bumpy.

*General appearance*.—Elliptical.

*Serration*.—Small and single.

*Undulation on the margin*.—Medium.

*Venation*.—Color is commonly near Yellow-Green Group 144A and pattern is imparipinnate.

*Petiole rachis*.—Color of upper surface: commonly near Yellow-Green Group 144A suffused with near Greyed-Purpled Group 178A. — color of under surface: commonly near Yellow-Green Group 144B. — texture: upper surface is slightly glandular, under surface has few prickles. — rachis of terminal leaflet: length is approximately 3.0 cm on average and diameter is typically less than 0.1 cm.

*Petioles*.—Upper surface: few glandular. — under surface: few prickles. — color of upper surface: commonly near Yellow-Green Group 144A more or less suffused with near Greyed-Purple Group 178A. — color of under surface: commonly near Yellow-Green Group 144B. — length: approximately 3.0 cm on average. — diameter approximately 0.2 cm on average.

*Stipules*.—Length: approximately 1.1 cm on average. — width: approximately 0.4 cm on average. — general appearance: rather broad. — texture: few prickles. — color of upper surface: commonly near Yellow-Green Group 145A more or less suffused with near Yellow-Green Group 144B. — color of under surface: commonly near Yellow-Green Group 145A more or less suffused with near Yellow-Green Group 144B.

Inflorescence:

*Number of flowers per stem*.—Typically between 1 to 7 flowers per stem.

*Lastingness of the bloom*.—On the plant: approximately 15 days on average. — in vase: not tested.

*Bud*.—Shape: conical. — size: medium. — length: approximately 3.0 cm on average. — width: approximately 2.0 cm on average. — color as calyx breaks: upper surface: commonly homogenous and continuous color gradient from near Orange Group 25A at the base to near Orange-Red Group 32A at the edge of the petal; basal spot is very little and color is commonly near Yellow Group 7A. under surface: commonly homogenous and continuous color gradient from near Orange Group 25A at the base to near Orange-Red Group 32A at the edge of the petal; basal spot is very little and color is commonly near Yellow Group 7A.

*Sepals*.—Number: commonly 5. — length: typically between 2.0 cm to 2.5 cm on average. — width: approximately 0.7 cm on average (on median part). — shape: at the top: elongate and narrow. at the base: flat at union with the receptacle. — extensions: typically 2 sepals without extensions, 1 sepal with weak extension, and 2 sepals with medium extensions. — upper surface: texture: tomentous. color: commonly near a color between Yellow-Green Group 144A and 144B completely covered by near White Group 155A hairs. — under surface: texture: slightly tomentous or slightly glandular depends on the sepals. color: commonly near a color between Yellow-Green Group 144A and 144B, slightly covered by near White Group 155A hairs on the edge.

*Receptacle*.—Color: commonly near Yellow-Green Group 144B. — length: approximately 1.0 cm on average. — width: approximately 1.0 cm on average. — surface: smooth. — shape: slightly pear shaped.

*Peduncle*.—Length: approximately 4.0 cm on average. — width: approximately 0.3 cm on average. — surface: smooth. — color: commonly near Yellow-Green Group 144B.

*Flower*.—Diameter when open: approximately 8.0 cm on average. — depth of the flower: typically between 2.5 cm to 3.5 cm. — shape: cup shaped. — shape when viewed from above: irregular rounded. — shape of the upper part of the flower profile: flattened convex. — shape of the lower part of the flower profile: flat. — type: double. — number of petals under normal conditions: typically between 20 to 25 petals. — petals: shape: obcordate (rounded with a very little tip at the top and acute at the base). texture: soft. length: typically between 3.0 cm to 4.0 cm. width: typically between 2.0 cm to 4.0 cm. — undulation of the petal: medium. — reflexing of the petal: very weak. — petal incision: absent. — petal arrangement: imbricated with petaloids; less than 5 petaloids per flower in general (very little deformed petal fused with a stamen). — petal drop: petals drop off cleanly before drying. — fragrance: very slightly sweet fragrance. — discoloration of the flower: yes (disappearance of yellow and orange pigments). — color when opening: basal spot on the upper surface: commonly near Yellow Group 5A. upper surface external petals: commonly a gradient color near Yellow Group 5A from the basal spot to near a color between Orange Group 29A and Red Group 38A to the edge of the petal. upper surface internal petals: commonly near Red Group 51B on the edge of the petal more and more amply suffused with near a color between Orange Group 24A and 25A when going to the base of the petal. basal spot on the under surface: commonly near Yellow Group 5B. under surface external petals: a gradient color near Yellow Group 5B from the basal spot to near a color between Orange Group 29B and Red Group 38B to the edge of the petal. under surface internal petals: commonly near Red Group 51C on the edge of the petal more and more amply suffused with near Orange Group 25B when going to the base of the petal. — color of the open flower: basal spot: absent. upper surface of the flower: commonly near Red-Purple Group 62C slightly suffused with near Red-Purple Group 62A. under surface of the flower: commonly near Red-Purple Group 65C slightly suffused with near Red-Purple Group 65A. — anthers: typically between 160 to 170, length is approximately 0.2 cm on average, width is approximately 0.1 cm on average, coloration is commonly near Yellow-Orange Group 22A, and arrangement is regular around styles. — filaments: length is approximately 0.5 cm on average and coloration is commonly near Red Group 50B. — styles: length is approximately 0.4 cm on average, coloration is commonly near Red Group 50B, and number is typically between 30 to 40. — stigmas: length is approximately 0.1 cm on average and coloration is commonly near Yellow-Orange Group 22A. — pollen: abundant; color is commonly near Yellow-Orange Group 22A. — hips: information not available.

Development:

*Vegetation*.—Very strong.

*Blooming*.—Very early in the season, abundant and nearly continuous, typically from May to November in France.

*USDA hardiness zone*.—At least Zone 5.

*Tolerance to disease*.—Exceptional, and particularly against rust (*Phragmidium* sp.), powdery mildew (*Podasphaera pannosa*), and black spot (*Diplocarpon rosae*).

The new 'MEICONFIZ' variety has not been observed under all possible environmental conditions to date. Accordingly, it is possible that the phenotypic expression may vary somewhat with changes in light intensity and duration, cultural practices, and other environmental conditions.

I claim:

1. A new and distinct variety of rose plant named 'MEICONFIZ' characterized by the following combination of characteristics:

(a) forms very nice orange colored flowers, (b) produces double flowers, and (c) exhibits a bushy growth habit;

substantially as herein shown and described.

* * * * *

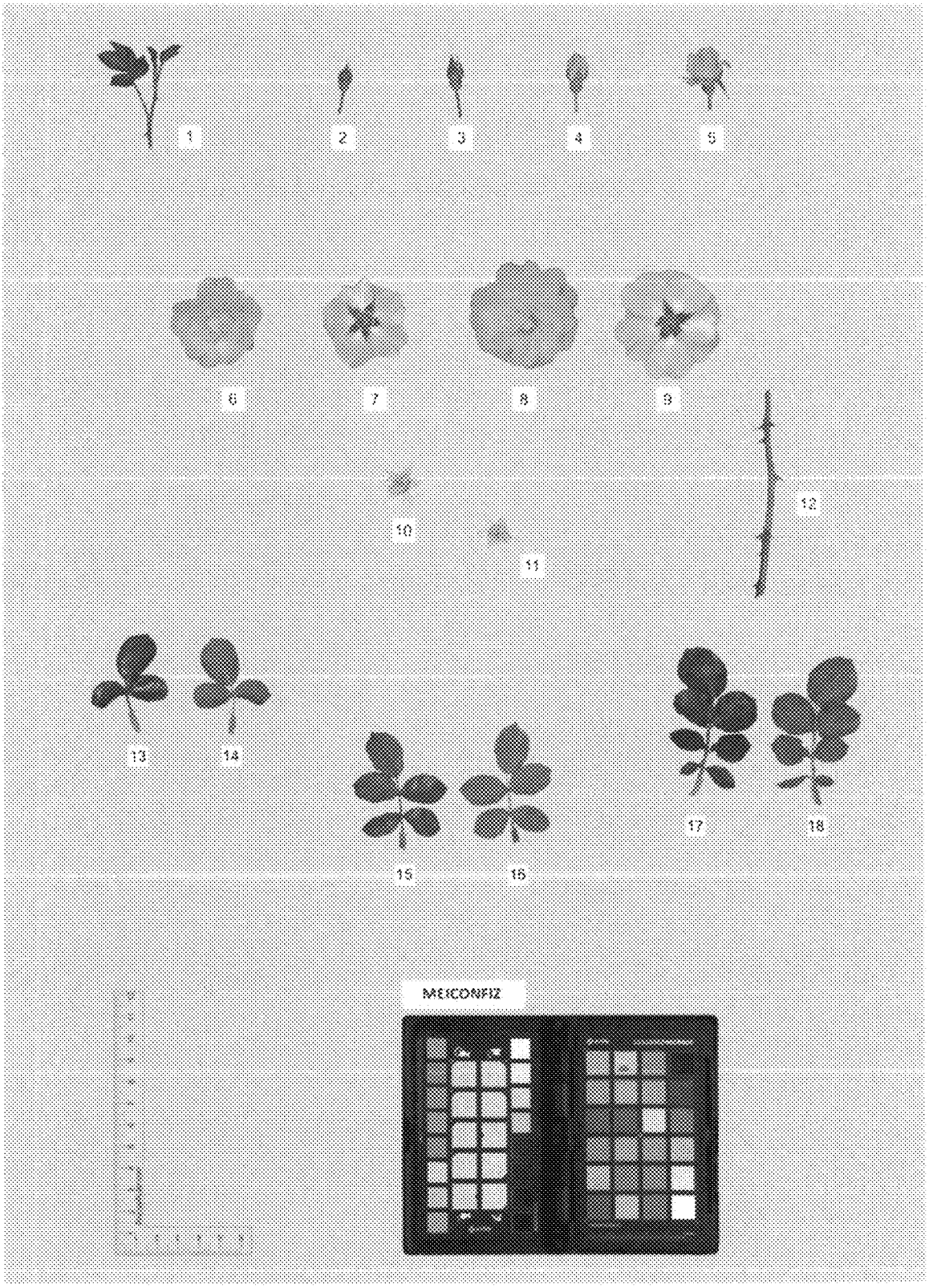
1
2
3
4
5
6
7
8
9
10
11
12
13
14
15
16
17
18
MEICONFIZ